US010797472B1

(12) United States Patent
Lee et al.

(10) Patent No.: US 10,797,472 B1
(45) Date of Patent: Oct. 6, 2020

(54) ELECTRON GENERATION APPARATUS CAPABLE OF MULTI-STAGE BOOSTING FOR VARIABLE CAPACITY

(71) Applicant: GROON CO., LTD., Jeollabuk-do (KR)

(72) Inventors: In Ho Lee, Jeollabuk-do (KR); Young Pyo Hong, Jeollabuk-do (KR); Ji Young Park, Jeollabuk-do (KR); Mun Gu Lee, Jeollabuk-do (KR); Tae Hun Lee, Jeollabuk-do (KR); Chan Young Park, Jeollabuk-do (KR); Gyeong Han Son, Jeollabuk-do (KR)

(73) Assignee: GROON CO., LTD., Jeollabuk-do (KR)

( * ) Notice: Subject to any disclaimer, the term of this patent is extended or adjusted under 35 U.S.C. 154(b) by 0 days.

(21) Appl. No.: 16/722,106

(22) Filed: Dec. 20, 2019

(30) Foreign Application Priority Data

Nov. 18, 2019 (KR) .......................... 10-2019-0147586
Nov. 18, 2019 (KR) .......................... 10-2019-0147593

(51) Int. Cl.
| | | |
|---|---|---|
| *C02F 1/00* | (2006.01) | |
| *H01T 19/04* | (2006.01) | |
| *C02F 1/46* | (2006.01) | |
| *H02M 3/335* | (2006.01) | |
| *H02M 7/06* | (2006.01) | |

(52) U.S. Cl.
CPC ............ *H01T 19/04* (2013.01); *C02F 1/4608* (2013.01); *C02F 2303/02* (2013.01); *H02M 3/33523* (2013.01); *H02M 7/06* (2013.01)

(58) Field of Classification Search
CPC .......... C02F 1/302; C02F 1/305; C02F 1/307; C02F 1/461; C02F 1/46114
See application file for complete search history.

(56) References Cited

U.S. PATENT DOCUMENTS

| | | | |
|---|---|---|---|
| 10,032,593 B1* | 7/2018 | Lee ........................ | C02F 1/4608 |
| 2004/0035798 A1* | 2/2004 | Holland .............. | C02F 1/46109 |
| | | | 210/695 |
| 2017/0283284 A1* | 10/2017 | Jung .................... | C02F 1/46109 |
| 2017/0362107 A1* | 12/2017 | Oinuma ................. | C01B 13/11 |
| 2018/0354823 A1* | 12/2018 | Lee ......................... | C02F 1/487 |
| 2019/0322552 A1* | 10/2019 | Nakayama .......... | C02F 1/46109 |

FOREIGN PATENT DOCUMENTS

| | | |
|---|---|---|
| KR | 10-0529749 | 11/2005 |
| KR | 10-1042141 | 6/2011 |

* cited by examiner

*Primary Examiner* — Tung X Le

(57) ABSTRACT

The present disclosure provides an electron generation apparatus includes: a discharge pin module having a support plate and a plurality of discharge pins coupled to the support plate; a discharge plate module disposed to be spaced apart from the plurality of discharge pins; a discharge plate slidably coupled inside the discharge plate module; a support structure having a coupling plate to which the discharge pin module and the discharge plate module are detachably coupled; and a circuit module having a main board located at a side opposite to the discharge pin module with the coupling plate being interposed therebetween and a plurality of distributed processing boards connected to the main board to apply a high-voltage, high-frequency pulse power to the plurality of discharge pins individually.

10 Claims, 5 Drawing Sheets

ELECTRON GENERATION APPARATUS CAPABLE OF MULTI-STAGE BOOSTING FOR VARIABLE CAPACITY

CROSS-REFERENCE TO RELATED APPLICATION

This application claims priority of Korean Patent Application No. 10-2019-0147586, filed on Nov. 18, 2019, and priority of Korean Patent Application No. 10-2019-0147593, filed on Nov. 18, 2019, in the KIPO (Korean Intellectual Property Office), the disclosure of which is incorporated herein entirely by reference.

BACKGROUND OF THE INVENTION

Field of the Invention

The present disclosure relates to an electron generation apparatus used for water treatment, pollutant treatment and odor removal, and more specifically, to an electron generation apparatus capable of multi-stage boosting for variable capacity to improve operation stability and power efficiency.

Description of the Related Art

Generally, the corona discharge method is representatively known as a method or structure that allows anion to be produced at atmospheric pressure. The corona discharge method has a structure that induces the generation of corona discharge between electrodes by applying a high voltage to the electrodes for each polarity.

The corona discharge generated as described above may be classified into a positive electrode corona and a negative electrode corona according to the conditions of the voltage applied to the electrodes for each polarity. The characteristics of the double positive electrode corona are easily expanded spatially than the negative electrode corona, but the negative electrode corona method generating a large number of free electrons and radicals is widely used in the field of industrial devices.

In addition, the method for generating free electrons, negative ions, and the like is classified into a pulse power supply method, an AC power supply method, a DC power supply method, and the like according to the type of a power supply device that applies power to each electrode. At this time, a conventional ozone generator or anion oxygen generator using pulse power has a pin-plate structure including a discharge pin and a ground portion. The plus electrode has a plate shape, and the minus electrode has a pin shape. Here, if a pulse power is applied to each electrode, a corona discharge is formed, and ozone or anion oxygen is generated at this time. However, the conventional power generator has a complicated structure for applying power to the plurality of discharge pins and the plurality of discharge pins respectively, which results in poor workability in replacing components.

In addition, the conventional electron generation apparatus has a limitation in practical use due to the durability problem and also has deteriorated efficiency in terms of power consumption.

SUMMARY OF THE INVENTION

The present disclosure is designed to solve the conventional problem, and the present disclosure is directed to providing an electron generation apparatus, which may facilitate the management of contamination generated during a discharge process by using a discharge plate slidably coupled to a discharge plate module of an electron generation unit and improve maintenance management using a simple power applying structure to ensure excellent workability.

In addition, the present disclosure is directed to providing an electron generation apparatus, which has improved stability and power efficiency by enabling multi-stage boosting for variable capacity.

In one general aspect, there is provided an electron generation apparatus, comprising: a discharge pin module having a support plate and a plurality of discharge pins coupled to the support plate; a discharge plate module disposed to be spaced apart from the plurality of discharge pins; a discharge plate slidably coupled inside the discharge plate module; a support structure having a coupling plate to which the discharge pin module and the discharge plate module are detachably coupled; and a circuit module having a main board located at a side opposite to the discharge pin module with the coupling plate being interposed therebetween and a plurality of distributed processing boards connected to the main board to apply a high-voltage, high-frequency pulse power to the plurality of discharge pins individually, wherein the plurality of distributed processing boards includes: a high-voltage boosting unit 1353 configured to boost an AC power; and a DC conversion unit connected to the high-voltage boosting unit to convert the boosted AC power into a DC power and perform half-wave rectification.

The electron generation apparatus according to the present disclosure as described above may facilitate the management of contamination generated during a discharge process by using a discharge plate slidably coupled to a discharge plate module of an electron generation unit and improve maintenance management using a simple power applying structure to ensure excellent workability.

In addition, the electron generation apparatus has improved stability and power efficiency by enabling multi-stage boosting for variable capacity.

BRIEF DESCRIPTION OF THE DRAWINGS

The above and other features and advantages will become more apparent to those of ordinary skill in the art by describing in detail exemplary embodiments with reference to the attached drawings, in which.

In the following description, the same or similar elements are labeled with the same or similar reference numbers.

DETAILED DESCRIPTION

Figure 1:
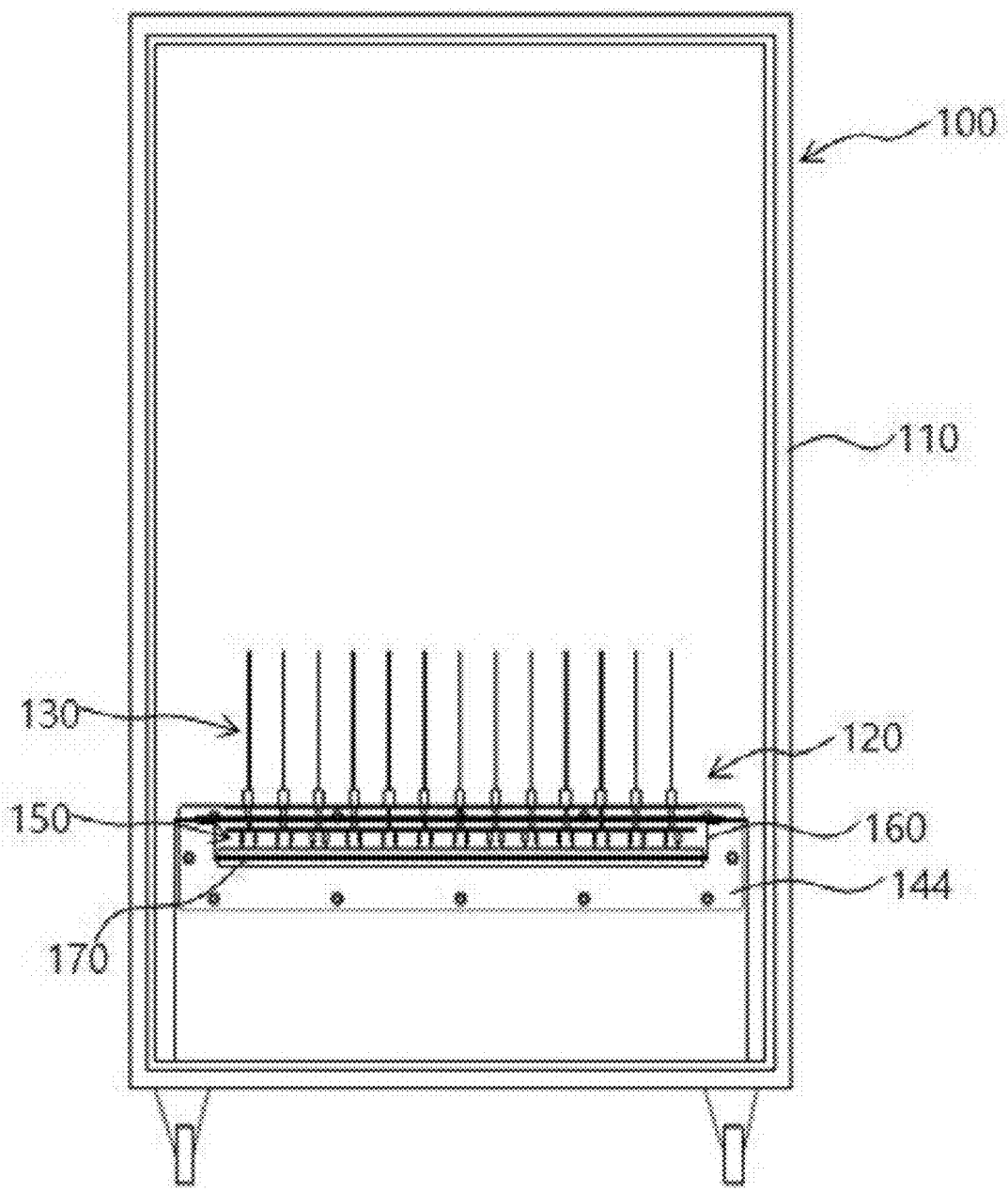
FIG. 1 is a side view showing an electron generation apparatus according to an embodiment of the present disclosure.

The present invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes", "comprises" and/or "comprising," when used in this specification, specify the presence of stated features, integers, steps, operations, elements, and/or components, but do not preclude the presence or addition of one or more other features, integers, steps, operations, elements, components, and/or groups thereof. In addition, a term such as a "unit", a "module", a "block" or like, when used in the specification, represents a unit that processes at least one function or operation, and the unit or the like may be implemented by hardware or software or a combination of hardware and software.

Reference herein to a layer formed "on" a substrate or other layer refers to a layer formed directly on top of the substrate or other layer or to an intermediate layer or intermediate layers formed on the substrate or other layer. It will also be understood by those skilled in the art that structures or shapes that are "adjacent" to other structures or shapes may have portions that overlap or are disposed below the adjacent features.

In this specification, the relative terms, such as "below", "above", "upper", "lower", "horizontal", and "vertical", may be used to describe the relationship of one component, layer, or region to another component, layer, or region, as shown in the accompanying drawings. It is to be understood that these terms are intended to encompass not only the directions indicated in the figures, but also the other directions of the elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Preferred embodiments will now be described more fully hereinafter with reference to the accompanying drawings. However, they may be embodied in different forms and should not be construed as limited to the embodiments set forth herein. Rather, these embodiments are provided so that this disclosure will be thorough and complete, and will fully convey the scope of the disclosure to those skilled in the art.

Hereinafter, an electron generation apparatus according to the present disclosure will be described with reference to FIGS. 1 to 4.

Figure 2:
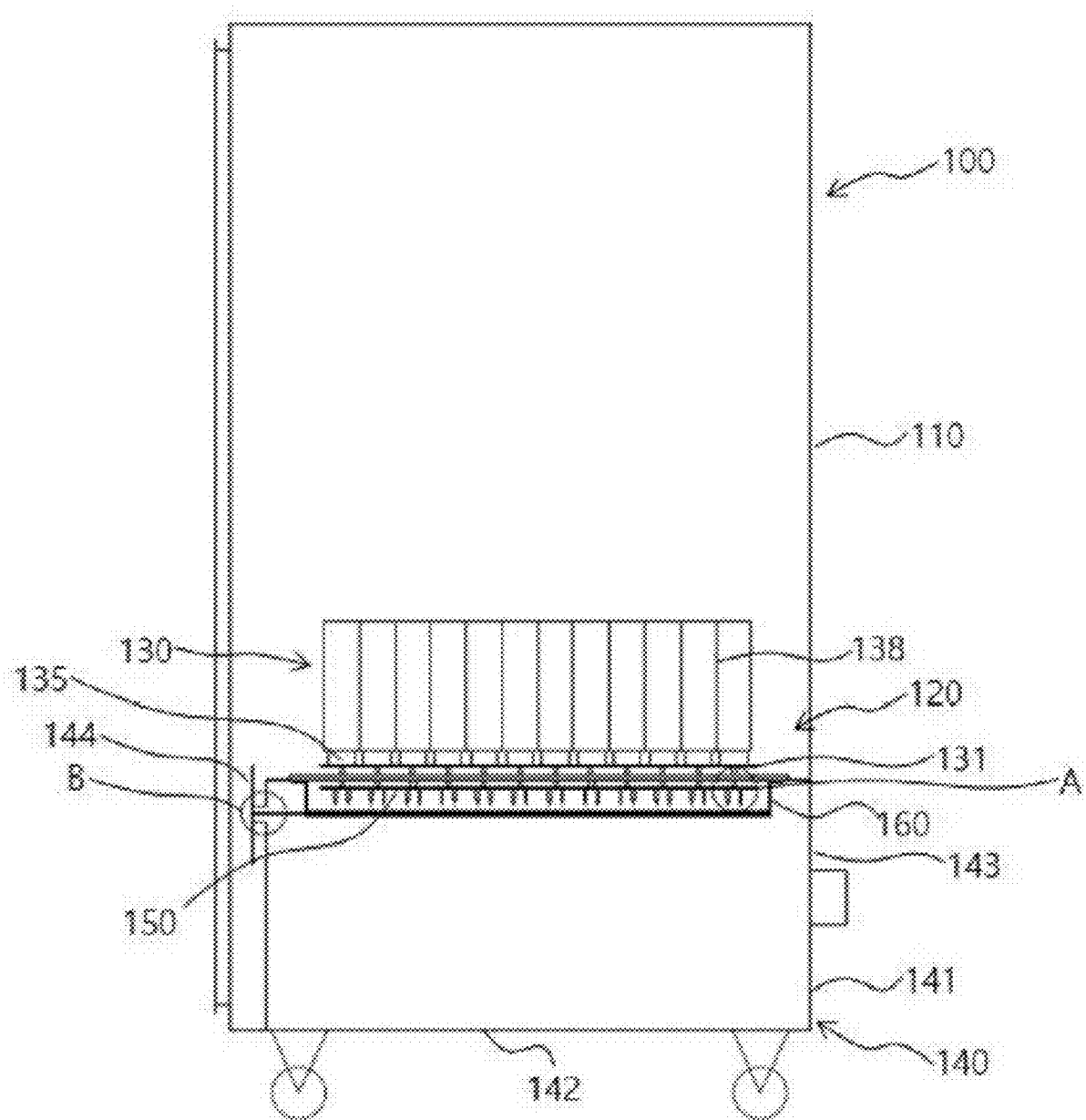
FIG. 2 is a front view showing the electron generation apparatus of FIG. 1.
Figure 3:
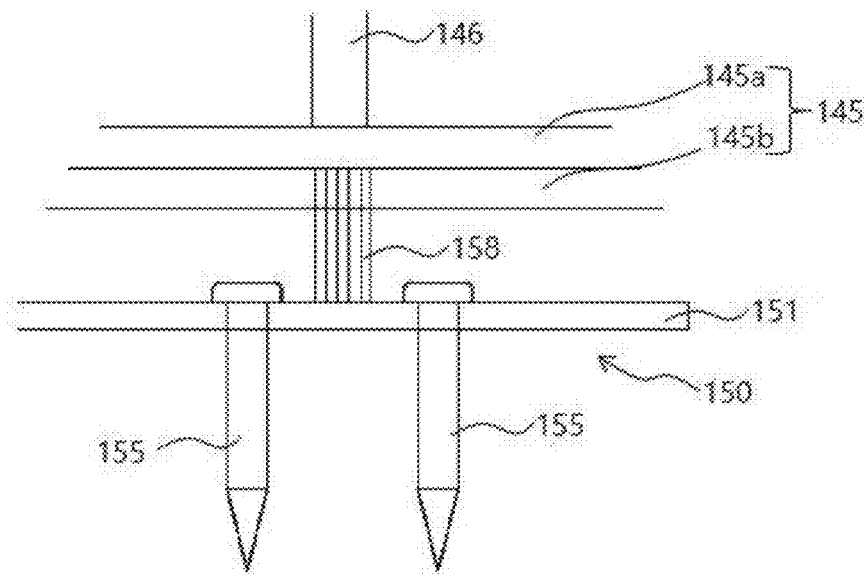
FIG. 3 is an enlarged view showing a portion 'A' of FIG. 2.
Figure 4:
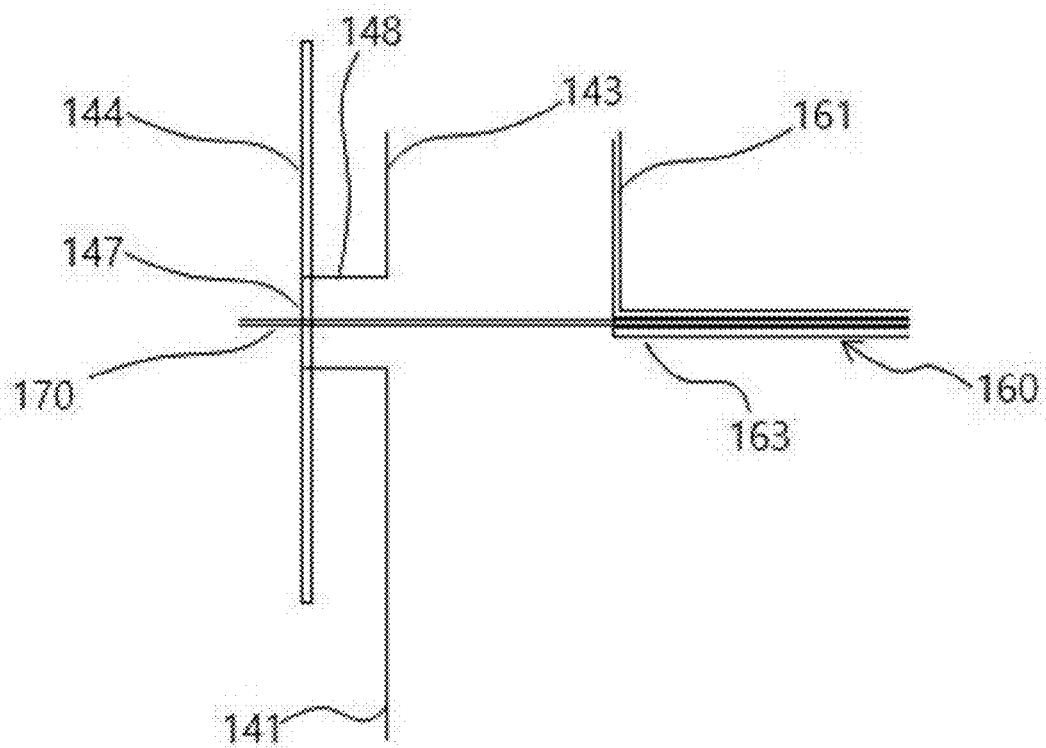
FIG. 4 is an enlarged view showing a portion 'B' of FIG. 2.

FIGS. 1 and 2 are a side view and a front view showing an interior of an electron generation apparatus according to an embodiment of the present disclosure.

The electron generation apparatus 100 includes an outer case 110 and an electron generation unit 120 received inside the outer case 110. Inside the outer case 110, a control unit for controlling the electron generation unit 120 and a power source for supplying power may be received together to be located at an upper portion of the electron generation unit 120.

The electron generation unit 120 includes a circuit module 130, a support structure 140 disposed at a lower portion of the circuit module 130, a discharge pin module 150 electrically connected to the circuit module 130, a discharge plate module 160 disposed to be spaced apart on a lower side of the discharge pin module 150, and a plurality of electromagnetic field generators disposed to be received in the support structure 140.

The circuit module 130 includes a main unit 131, a plurality of distributed processing boards 135 connected to the main board 131, and a coupling unit 138 functioning to fasten the plurality of distributed processing boards 135.

The main board 131 generally has a flat plate shape and includes a plurality of connectors to which the plurality of distributed processing boards 135 are connected. The plurality of connectors is located on the main board 131 to be spaced apart from each other along transverse and longitudinal directions. The distributed processing boards 135 are located on the upper surface of the main board 131.

Each of the plurality of distributed processing boards 135 includes an independent high-voltage and high-frequency pulse conversion circuit to apply a high-voltage and high-frequency pulse power individually. Each of the plurality of distributed processing boards 135 is connected to the connector provided at the main board 131 at the upper surface of the main board 131.

The main board 131 and the plurality of distributed processing boards 135 connected to the main board 131 keep firmly coupled by the coupling unit 138 to form an integrated circuit module 130.

The circuit module 130 is detachably coupled to the support structure 140.

Specific implementation of the circuit module 130 and control flow thereof will be described later in detail with reference to FIGS. 5 and 6.

The support structure 140 includes a body 141 and a coupling plate 145 detachably coupled on an open upper portion of the body 141.

The body 141 includes a bottom plate 142, a sidewall 143 formed to extend from the bottom plate 142, and a flange 144 formed to extend outward from an upper side of the sidewall 143.

A plurality of electromagnetic field generators is installed to the bottom plate 142 and the sidewall 143 and located in the inner space of the body 141. In the inner space of the body 141, electrons are moved from top to bottom by the plurality of electromagnetic field generators. The coupling plate 145 is detachably coupled by a coupling unit such as a screw to cover the open upper portion of the body 141.

The circuit module 130, the discharge pin module 150 and the discharge plate module 160 are detachably coupled onto the coupling plate 145. The circuit module 130 is located outside the support structure 140 with the coupling plate 145 being interposed therebetween, and the discharge pin module 150 and the discharge plate module 160 are located in the inner space of the body 141.

The coupling plate 145 is made of an electrical insulating material, and a plurality of connection protrusions 146 formed in one-to-one correspondence with the distributed processing boards 135 may be installed at the coupling plate 145. The connection protrusion 146 is formed to protrude from the coupling plate 145 toward the corresponding distributed processing board 135 and is made of an electrically conductive material.

Meanwhile, the fastening protrusion 158 functions to detachably couple the coupling plate 145 and the discharge pin module 150. That is, the connection protrusion 146 and the fastening protrusion 158 are formed to be exposed along the vertical direction with respect to the coupling plate 145.

Through the connection protrusion 146 and the fastening protrusion 158, electricity from the corresponding distributed processing board 135 is applied to the discharge pin module 150.

The coupling plate 145 is configured such that a pair of coupling plate are stepped along upper and lower portions. Specifically, the coupling plate 145 includes an upper coupling plate 145a connected to the circuit module 130 through the connection protrusion 146 and a lower coupling plate 145b connected to the support plate 151 of the discharge pin module 150 through the fastening protrusion 158. The lower coupling plate 145b has a structure covering the open upper portion of the body 141 in a state of being connected to the upper end of the support plate 151 of the discharge pin module 150. Meanwhile, the upper coupling plate 145a is formed to maintain a smaller width than the lower coupling plate, thereby forming a stepped shape. Specifically, the upper coupling plate 145a may be in the form of a PCB coupling plate, and the lower coupling plate 145b may be in the form of an STS discharging rectangular box.

Since the coupling plate 145 is configured by stacking a pair of coupling plates, the coupling plate may be replaced easily while maintaining a light weight, compared to a conventional single coupling plate. In addition, it is possible to reduce the generation of induction current that may occur at a side end of the coupling plate 145 by stacking a plurality of coupling plates made of different materials.

The flange 144 is coupled to communicate with the inner space of the body 141 in an upper region of the sidewall 143. That is, in the basic structure of the rectangular plate, a flange passing hole 147 having a predetermined width is formed along the length direction. A flange protrusion 148 is formed along an inner edge of the flange passing hole toward the discharge plate module 160. That is, the flange 144 allows the discharge plate 170, which is slidably coupled to the discharge plate module 160, to be drawn out through the flange passing hole 147, in a state of being coupled to the sidewall 143 by means of the flange protrusion.

In the present disclosure, it is possible to periodically manage dust, which may be collected on the discharge plate module 160, by using the discharge plate 170. That is, in the existing technique, since impurity particles collected in the region of the discharge plate module 160 during the discharge process are accumulated, the function of the discharge plate is eventually not performed due to the dust, and at the same time, the entire device needs to be repaired. For this reason, the discharge plate 170 is configured to be drawn out through one side of the lower end of the discharge plate module 160, thereby facilitating replacement and cleaning the discharge plate 170.

The discharge pin module 150 includes a support plate 151 and a plurality of discharge pins 155 coupled to the support plate 151.

The support plate 151 generally has a flat plate shape and is located at a side opposite to the main board 131 with the coupling plate 145 being interposed therebetween to be spaced apart from the coupling plate 145. The support plate 151 is made of an electrical insulating material. The plurality of discharge pins 155 are coupled to the support plate 151.

The plurality of discharge pins 155 protrude from the support plate 151 in a direction opposite to the coupling plate 145 in a state of penetrating the support plate 151 from top to bottom. The discharge pin 155 is made of an electric conducting material, and in an embodiment, the discharge pin 155 may be formed by coupling a screw to the support plate 151. In the screw serving as the discharge pin 155, a head is located at the coupling plate 145, and an elongated body protrudes in the opposite direction.

Among the plurality of discharge pins 155, neighboring discharge pins 155 form a single discharge pin group in which the discharge pins are electrically connected. In this embodiment, one discharge pin group includes four discharge pins 155, but the present disclosure is not limited thereto. Four discharge pins 155 forming the discharge pin group are electrically connected to each other by an electric conductive member (not shown). The electric conductive member is connected to the connection protrusion extending from the lower end of the coupling plate 145 while keeping connected to the four discharge pins 155 at the upper end of the support plate 151.

A high voltage is applied to the single discharge pin group from one corresponding distributed processing board 135. The four discharge pins 155 forming a single discharge pin group are electrically connected.

The discharge plate module 160 generally has a flat plate shape and is made of an electrically conductive material. The discharge plate module 160 is located to be spaced apart from the plurality of discharge pins 155 by a predetermined distance in the inner space of the body 141 of the support structure 140.

The discharge plate module 160 includes a bent portion 161 fastened to a lower end of the coupling plate 145 and a discharge plate receiving portion 163 coupled to a lower end of the bent portion. In a state where the discharge plate receiving portion 163 has a height corresponding to the flange protrusion 148 of the flange 144, one side of the discharge plate receiving portion facing the flange protrusion is opened, and the other side of the discharge plate receiving portion is closed to correspond to an entry limit point of the discharge plate that enters the discharge plate receiving portion.

The discharge plate module 160 is detachably coupled to the coupling plate 145 by a coupling unit together with the discharge pin module 150. As corona discharge is generated between the discharge pin 155 and the discharge plate module 160, electrons and radicals ionized from the discharge pin 155 serving as a minus electrode to the discharge plate module 160 serving as a plus electrode are emitted.

The discharge plate 170 has a plurality of perforation holes located at the shortest distance respectively corresponding to the plurality of discharge pins 155 in one-to-one relationship. The perforation hole maintains the shortest discharge distance to improve discharge efficiency when foreign substances such as dust emitted from the discharge pin 155 are accumulated on the discharge plate 170 at the beginning of discharge.

The plurality of electromagnetic field generators is installed at the bottom plate 142 and the sidewall 143 of the body 141, respectively, to transfer the electrons and radicals emitted from the discharge pin 155 to the bottom plate 142. Each of the plurality of electromagnetic field generators may include a galvanized steel core and a coil wound around the core, and any configuration capable of generating an electromagnetic field may be used.

Figure 5:
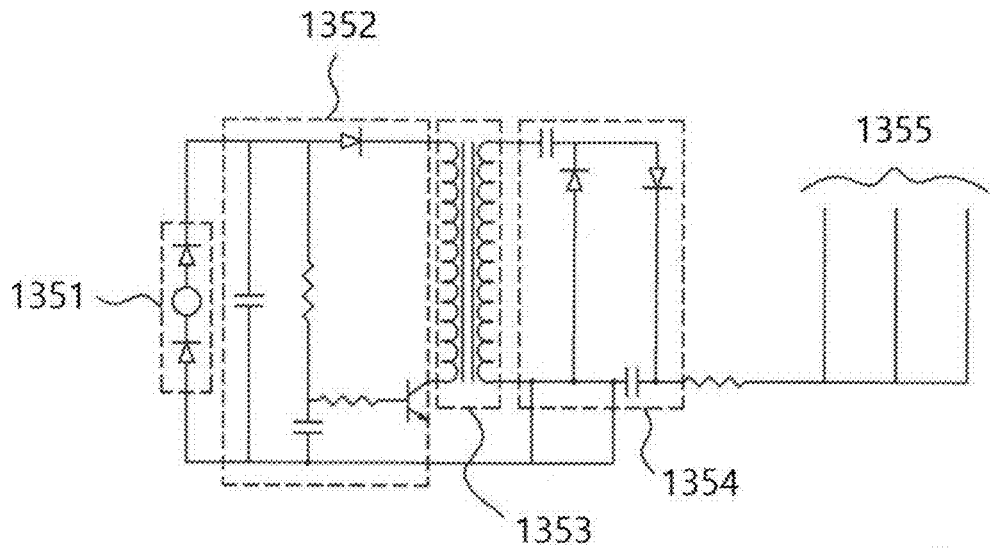
FIG. 5 is a circuit diagram showing a circuit module according to an embodiment of the present disclosure.
Figure 6:
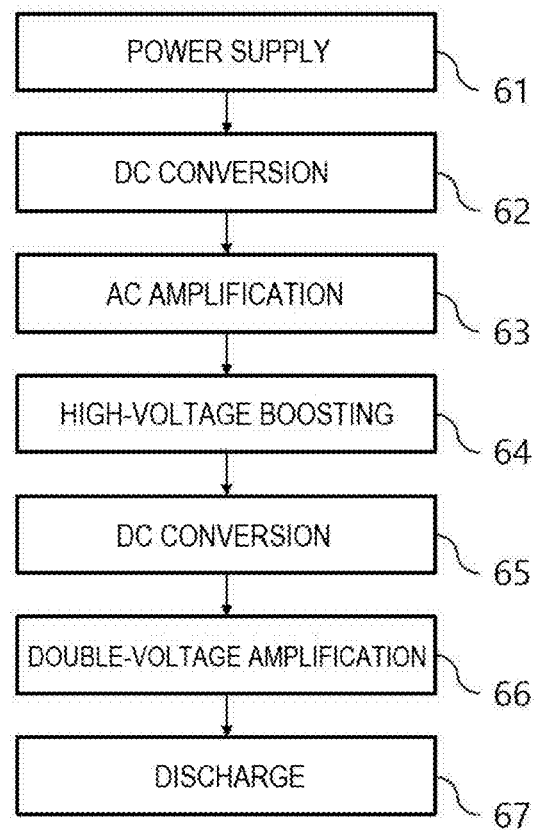
FIG. 6 is a flowchart for illustrating an operation flow of the circuit module of FIG. 5.

FIG. 5 is a circuit diagram showing a circuit module according to an embodiment of the present disclosure, and FIG. 6 is a flowchart for illustrating an operation flow of the circuit module of FIG. 5, which shows an example implementing the circuit of the distributed processing board included in the circuit module.

Each distributed processing board 135 may include a conversion unit 1351, an amplification unit 1352, a high-voltage boosting unit 1353 and a DC conversion unit 1354.

An AC power supplied from a power source is applied to conversion unit 1351 (Step 61), and accordingly the conversion unit 1351 converts the applied AC power to a DC power (Step 62).

The amplification unit 1352 amplifies the DC power converted by the conversion unit 1351 and converts the DC power to an AC power again (Step 63).

The high-voltage boosting unit 1353 boosts the AC power amplified and converted by the amplification unit 1352 (Step 64). Accordingly, a potential is formed at the plurality of discharge pins 155. As the potential increases, supersaturation of electrons may be induced. In addition, a shielding structure may be formed on the surface of the high-voltage boosting unit 1353. For example, an insulating plastic resin material may be molded on the surface of the high-voltage boosting unit 1353 to form a shielding structure. This is in preparation for the voltage to be reversed to the high-voltage boosting unit 1353 due to the closed loop of the positive electrode wire, explained later.

The DC conversion unit 1354 is connected to the high-voltage boosting unit 1353 to convert the boosted AC current into a DC current and perform half-wave rectification thereto (Step 65). Here, the DC conversion unit 1354 is configured such that a plurality of diode and capacitor pairs are connected in parallel to convert the AC current in multiple stages. Accordingly, it is possible to perform multi-stage boosting. As a result, capacity may be freely changed to optimize power efficiency.

In addition, double-voltage amplification and half-wave rectification are simultaneously performed at the capacitor, and the discharge pin 1355 is connected to a negative electrode wire connected to the capacitor (Step 66). Accordingly, the current amplified doubly at the capacitor is applied to the discharge pin 1355 (Step 67).

Meanwhile, due to the closed loop of the positive electrode wire, a large potential difference is formed at the negative electrode wire and the discharge pin 1355 from the air, and the current may be concentrated on the discharge pin 1355 through the negative electrode wire to induce an oversaturation state of electrons.

Figure 7:
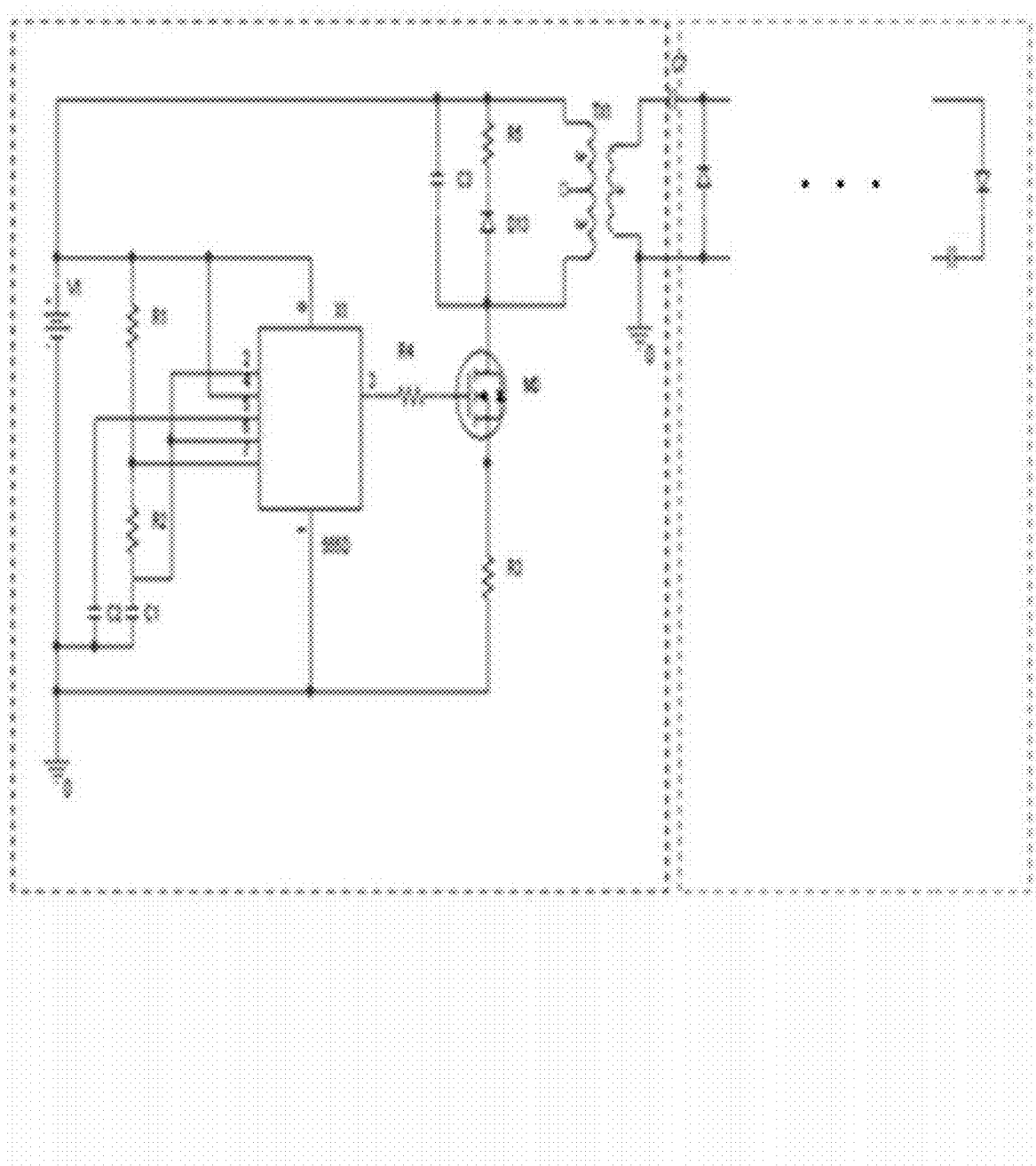
FIG. 7 is a circuit diagram showing a circuit module according to another embodiment of the present disclosure.

FIG. 7 is a circuit diagram showing a circuit module according to another embodiment of the present disclosure, where a red dotted line on the left represents a pulse generator and a circuit portion that performs AC voltage amplification and conversion, and a blue dotted line on the right represents a circuit portion that boosts in multi stages.

Each stage of the multi-stage booster circuit portion is configured using two diodes and two capacitors and is configured to output a half-wave rectified DC power.

While the present disclosure has been described with reference to the embodiments illustrated in the figures, the embodiments are merely examples, and it will be understood by those skilled in the art that various changes in form and other embodiments equivalent thereto can be performed. Therefore, the technical scope of the disclosure is defined by the technical idea of the appended claims The drawings and the forgoing description gave examples of the present invention. The scope of the present invention, however, is by no means limited by these specific examples. Numerous variations, whether explicitly given in the specification or not, such as differences in structure, dimension, and use of material, are possible. The scope of the invention is at least as broad as given by the following claims.

What is claimed is:

1. An electron generation apparatus, comprising:
   a discharge pin module having a support plate and a plurality of discharge pins coupled to the support plate;
   a discharge plate module disposed to be spaced apart from the plurality of discharge pins;
   a discharge plate slidably coupled inside the discharge plate module;
   a support structure having a coupling plate to where the discharge pin module and the discharge plate module are detachably coupled; and
   a circuit module having a main board located at a side opposite to the discharge pin module with the coupling plate being interposed therebetween and a plurality of distributed processing boards connected to the main board to apply a high-voltage, high-frequency pulse power to the plurality of discharge pins individually,
   wherein the plurality of distributed processing boards comprising:
      a high-voltage boosting unit configured to boost an AC power; and
      a DC conversion unit connected to the high-voltage boosting unit to convert the boosted AC power into a DC power and perform half-wave rectification.

2. The electron generation apparatus of claim 1, wherein the DC conversion unit includes a plurality of diode and capacitor pairs connected in parallel to convert the AC power in multi stages.

3. The electron generation apparatus of claim 1, wherein the discharge plate module includes a bent portion fastened to a lower end of the coupling plate and a discharge plate receiving portion coupled to a lower end of the bent portion.

4. The electron generation apparatus of claim 1,
   wherein the support structure includes a body having an open upper portion and giving an inner space for receiving the discharge pin module and the discharge plate module, and the body includes a bottom plate, a sidewall formed to extend from the bottom plate and a flange formed to extend outward from an upper side of the sidewall,
   wherein the flange allows the discharge plate slidably coupled to the discharge plate module to be drawn out through a flange passing hole by means of a flange protrusion.

5. An electron generation apparatus, comprising:
   a main board having a plurality of connectors disposed on an upper surface thereof to be spaced apart from each other;
   a plurality of distributed processing boards respectively connected to the plurality of connectors so that a high-voltage, high-frequency pulse conversion circuit is mounted thereto; and
   a coupling unit configured to fasten the plurality of distributed processing boards,
   wherein each of the distributed processing boards comprising:
      an amplification unit configured to amplify a DC power and convert into an AC power;
      a high-voltage boosting unit configured to boost the AC power converted by the amplification unit; and
      a DC conversion unit connected to the high-voltage boosting unit to convert the boosted AC power into a DC power and perform half-wave rectification,
      wherein the DC conversion unit includes a plurality of diode and capacitor pairs connected in parallel to convert the AC power in multi stages.

6. An electron generation apparatus, comprising:
a discharge pin module having a support plate and a plurality of discharge pins coupled to the support plate;
a discharge plate module disposed to be spaced apart from the plurality of discharge pins;
a discharge plate slidably coupled inside the discharge plate module;
a support structure having a coupling plate to where the discharge pin module and the discharge plate module are detachably coupled; and
a circuit module having a main board located at a side opposite to the discharge pin module with the coupling plate being interposed therebetween and a plurality of distributed processing boards connected to the main board to apply a high-voltage, high-frequency pulse power to the plurality of discharge pins individually,
wherein the discharge plate module includes a bent portion fastened to a lower end of the coupling plate and a discharge plate receiving portion coupled to a lower end of the bent portion.

7. The electron generation apparatus of claim 6,
wherein the support structure includes a body having an open upper portion and giving an inner space for receiving the discharge pin module and the discharge plate module, and the body includes a bottom plate, a sidewall formed to extend from the bottom plate and a flange formed to extend outward from an upper side of the sidewall,
wherein the flange allows the discharge plate slidably coupled to the discharge plate module to be drawn out through a flange passing hole in a state of being coupled onto the sidewall by means of a flange protrusion.

8. The electron generation apparatus of claim 6, wherein the discharge plate has a plurality of perforation holes respectively formed corresponding to the plurality of discharge pins.

9. The electron generation apparatus of claim 6, wherein the coupling plate is coupled to the body to cover the open upper portion of the body.

10. The electron generation apparatus of claim 6, wherein the plurality of distributed processing boards comprising:
a high-voltage boosting unit configured to boost an AC power; and
a DC conversion unit connected to the high-voltage boosting unit to convert the boosted AC power into a DC power and perform half-wave rectification, the DC conversion unit includes a plurality of diode and capacitor pairs connected in parallel to convert the AC power in multi stages.

* * * * *